United States Patent [19]

Moro et al.

[11] Patent Number: 4,746,516

[45] Date of Patent: May 24, 1988

[54] PHARMACEUTICAL COMPOSITIONS CONSISTING OR CONSISTING ESSENTIALLY OF FREEZE-DRIED DRUG-CARRYING LIPOSOMES

[75] Inventors: Luigi Moro, Cairate; Guido Neri; Alessandro Rigamonti, both of Milan, all of Italy

[73] Assignee: Farmitalia Carlo Erba S.p.A., Milan, Italy

[21] Appl. No.: 921,856

[22] Filed: Oct. 22, 1986

Related U.S. Application Data

[63] Continuation of Ser. No. 712,447, Mar. 18, 1985, abandoned, which is a continuation-in-part of Ser. No. 596,846, Apr. 4, 1984, abandoned, which is a continuation of Ser. No. 111,837, Jan. 4, 1980, Pat. No. 4,460,577, which is a continuation-in-part of Ser. No. 945,515, Sep. 25, 1978, abandoned.

[51] Int. Cl.$^4$ .................. A61K 9/10; A61K 31/74; A61K 31/70
[52] U.S. Cl. .................. 424/450; 424/79; 514/34; 514/36
[58] Field of Search .................. 424/79, 450; 514/34, 514/36

[56] References Cited

U.S. PATENT DOCUMENTS

| | | | |
|---|---|---|---|
| 3,398,092 | 8/1968 | Fields | 424/79 |
| 3,794,584 | 2/1974 | Kunin | 424/79 |
| 3,887,698 | 6/1975 | McConnell | 424/12 |
| 4,016,100 | 4/1977 | Suzuki | 424/36 |
| 4,131,544 | 12/1978 | Elahi | 23/230 B |
| 4,145,304 | 3/1979 | Melnick | 424/79 |
| 4,229,360 | 10/1980 | Schneider | 424/36 |
| 4,298,594 | 11/1981 | Sears | 424/78 |

FOREIGN PATENT DOCUMENTS

| | | | |
|---|---|---|---|
| 2249552 | 10/1972 | Fed. Rep. of Germany | 424/14 |
| 51-26213 | 3/1976 | Japan | 424/19 |

OTHER PUBLICATIONS

Segal, Clin. Sci. & Mol. Med., 49:99–106, 1975.
Merck Index, 9th Ed., 1976, No. 3428.
Tritton, Biochem. & Biophys. Res. Comm., 84:802–808, 1978.
Tyrrell, Biochem. & Biophys., Acta 457:259–274, 1976.
F. J. T. Fildes (I.C.I), "Liposomes: From Physical Structure to Therapeutic Applications", 1981—475 to 477.
Juliano, R. L. et al., BBA, 770, 1984, 109 to 114.
Juliano, R. L. et al., Bio/Technology, Dec. 1983, 882 to 885.
Puisieux F., Labo-Pharma Probl. Tech., 30 (1982), No. 318, 133 to 151.
Weinstein, J. N. and Leserman, L. D., Pharmac. Ther., 24 (1984), 207 to 233.
Rao, L. S., "Liposomal Dosage Forms Development—Some Practical Considerations", J. Parent Sci. Tech., 37 (1983), No. 3, 72 to 75.
Weinstein, J. N., Cancer Treatment Reports, 68 (1984), 127 to 135.

*Primary Examiner*—J. R. Brown
*Assistant Examiner*—John W. Rollins, Jr.
*Attorney, Agent, or Firm*—Stevens, Davis, Miller & Mosher

[57] ABSTRACT

A method is disclosed for purifying non-homogeneous systems, known as liposomic suspensions, from non-entrapped drugs wherein said suspensions are treated with liquid or solid polymers of synthetic and organic nature having chemical functionality, which are used as ion-exchangers. The liquid or solid polymers are based on styrene, divinylbenzene, acrylic acid, methacrylic acid, and the like, normally known as ion-exchange resins, and may include carboxylic, phosphonic or sulphonic functions of different matrices. The ion-exchange resins may also include salified quaternary ammonium, primary, secondary and tertiary amminic or phosphinic functions or other functions with different matrices, including phenolformaldehyde, styrene-divinylbenzene, acrylates, methacrylates, hydrocarbons and condensation-resins. Treatment may also be carried out with polymers, copolymers, or mixtures thereof, not having any specific chemical function and which normally, but not exclusively, react according to Van der Waals' forces, commonly known as adsorbents. The invention also includes freeze-dried pharmaceutical compositions consisting or consisting essentially of lyophilic liposomes of drugs, such as doxorubicin hydrochloride, aminosidine sulphate or 5-fluoro-uracil. The pharmaceutical compositions are characterized by a high degree of stability.

2 Claims, No Drawings

PHARMACEUTICAL COMPOSITIONS CONSISTING OR CONSISTING ESSENTIALLY OF FREEZE-DRIED DRUG-CARRYING LIPOSOMES

This application is a continuation of application Ser. No. 712,447, filed 3-18-85, now abandoned, which in turn is a continuation-in-part of application Ser. No. 596,846 filed on 4-4-84, now abandoned, which in turn is a continuation of application Ser. No. 111,837, filed 1-4-80 and now U.S. Pat. No. 4,460,577, which in turn is a continuation-in-part of application Ser. No. 945,515, filed 9-25-78, and now abandoned. See also our copending application Ser. No. 678,013, filed 12-4-84.

The present invention relates to pharmaceutical compositions (lyophilic liposomes) and to processes for their preparation and purification.

More particularly, the invention relates to a new method for purifying liposomic suspensions obtained according to per se known methods and for stabilizing same by lyophilization.

Liposomes are pharmaceutical compositions in which the drug is either dispersed or variously present in corpuscles consisting of aqueous concentric layers adherent to lipidic layers (hydrophobic). The drug may be present both in the aqueous layer and in the lipidic layer (inside or outside) or, in any event, in the non-homogeneous system generally known as a liposomic suspension.

The hydrophobic layer generally, but not exclusively, comprises phospholipids such as lecithin and sphingomyelin, steorids such as cholesterol, more or less ionic surface active substances such as dicetylphosphate, stearylamine or phosphatidic acid, and/or other materials of a hydrophobic nature.

The diameters of the liposomes generally range from 15 nm to 5$\mu$.

The preparation or process generally carried out according to the known art comprises two main steps: the preparation of the liposomes and the purification of same from non-entrapped drug.

(1) Preparation of the liposomes: the lipidic or lipophilic components are dissolved in a suitable solvent which is then evaporated to dryness, generally under vacuum. The aqueous layer containing the drug is added to the flask containing the residue as a thin layer and the whole is submitted to mechanical or ultrasonic shaking for a time ranging from 10 seconds to several hours. The non-homogeneous layer so obtained (generally indicated as a liposomic suspension) must be purified from the non-entrapped drug.

(2) Separation of the liposomes from the non-entrapped drug: this procedure is usually carried out by elution on a chromatographic column using resins having an exclusively molecular sieve function, such as Sepharose 2B, 4B or 6B, or the like.

Liposomes are first recovered while the free drug is retained by the resin.

Another method is ultracentrifugation at 100,000 g and subsequent washing, always by ultracentrifugation, with a buffered solution. Still another method also used is dialysis.

The present invention relates to a new purification process for the non-homogeneous layer known as liposomic suspension by means of both liquid and solid polymers, which are of synthetic or organic nature with chemical functionality, which can be used as ion-exchangers, such as, for example, those based on styrene, divinylbenzene, acrylic or methacrylic acid, and usually known as ion-exchange resins.

A predetermined quantity of one or more of these resins is introduced directly into the flask containing the liposomic suspension to be purified, and this is submitted to shaking for 10 to 60 minutes. After filtration through a sintered glass filter able to retain the ion-exchange resin on which the non-entrapped drug has been absorbed, the liposomic pure suspension is obtained, which then may be submitted to lyophilization.

This purification procedure of the liposomic suspensions with ion-exchange resins show the great advantage of maintaining highly concentrated liposomic suspensions (e.g., up to 5 mg/ml of doxorubicin HCl), which cannot be maintained by chromatography on a molecular sieve (max 0.3 mg/ml). The liposomic suspension thus obtained is very stable and is not inclined to sediment or settle-out, unlike those obtained by ultracentrifugation.

The same result is achieved by employing, instead of ion-exchange resins, polymers and copolymers with no specific chemical function and which normally, but not exclusively, react according to Van der Waals' forces, generally known as adsorbent resins. These resins can be employed in the purification of liposomic suspensions, owing to the difference of polarity between the hydrophobic substances forming the liposomic shell and the drugs of a more or less hydrophilic nature.

The final chemical stabilization is achieved by lyophilization of the liposomic suspension.

The important novel characteristics of the products of the present invention are, in fact, the long-term stability and the maintenance of the physical integrity of both structure and drug. These result from having a formulation able to resist drug diffusion between lipidic walls, thus minimizing drug leakage outside the liposomic structure, and by preserving the lipidic component from oxidation and peroxidation, reactions that could promote leakage of drug and, in addition, could enhance degradation of the entrapped chemicals. Minor components have shown themselves able to prevent these phenomena not only in liposome formulation. Those skilled in the art successfully use these minor components, such as antioxidant, chelating agents, preservatives and so on, as commonly-named excipients.

In liposome formulation, the role of the excipient is generally that of maintaining the chemical and physical characteristics of the resulting product, and thus preventing physical damage to the structure, chemical degradation of the drug and its lipidic envelopment, as well as lamellar fusion or size enlargement.

In the freeze-dried liposome, the excipient should also provide a defense from thermal shocks due to the process, that is to balance the supercooling effect and the resulting osmotic stress. In addition, the presence of a hydrophilic support as excipient makes easier the reconstitution of the original suspension by the addition of water.

Several classes of chemical substances are well known under the term "excipient", but in liposome formulation one can divide the components according to their affinity for the solvent in which they have to be dissolved as follows:

active drug substance
liposomic wall components
hydrophilic excipients.

The liposomic wall components are generally but not exclusively selected from the following:

phospholipids, such as lecithin or sphingomyelin or phosphatidylcholine derivatives;

steroids, such as cholesterol;

surfactant substances, such as dicetylphosphate or stearylamine;

fat preservatives or anti-oxidant or antiperoxidant agents, such as alpha-, beta- and gamma-tocoferols and their derivatives (such as Vitamin E Acetate).

The hydrophilic excipients are generally but not exclusively selected from the following:

complexing agents with chelating functions for metallic ions, such as EDTA (ethylenediaminotetraacetic acid) or its salts;

buffering salts, such as phosphates or Tris (trimethylaminomethane);

preservatives (such as paraben);

physical supports to improve the tonicity of the suspension, such as sucrose, galactose, mannitol, albumin, polyethyleneglycol, dextran, lactose, maltose, polyvinylpyrrolidone, glycine, sodium chloride.

The active drug substance may be added to a group or to another one according to its solubility. When the drug is doxorubicin HCl, it is solubilized in the aqueous buffered solution.

The following examples are given for illustrative purposes in order still better to demonstrate the invention and its advantages:

EXAMPLE 1

In a saponification flask, the following quantitites of lipids were dissolved in chloroform and evaporated under vacuum to dryness: 1.5 g of egg lecithin, 0.4 g of cholesterol, and 0.2 g of dicetylphosphate.

A solution of doxorubicin hydrochloride (at a concentration of 10 mg/ml) was poured into the flask, in buffer phosphate 0.007N, and the suspension subjected to ultrasonic shaking for 1 minute.

The suspension was allowed to stand for 30 minutes at room temperature under nitrogen, whereupon 2 g of a resin, previously activated in sodium form, obtained by polymerization of methylmethacrylate properly "cross-linked" with a chemical reagent, such as divinylbenzene, with carboxylic functionality and macroreticular structure, which allows its use also in hydrophobic solutions, and commercially known by the trademark "IRC-50 and produced by Rohm and Haas, were then added (weight refers to dry weight and is equivalent to 5 ml of inflated or swollen resin).

The flask was subjected for about 30 minutes to shaking and then the suspension was filtered through a G 1 porous sheet of filter material.

Liposomes of size varying from 0.5 to $2\mu$ and containing about 60% of the starting amount of doxorubicin so obtained were stabilized by lyophilization.

EXAMPLE 2

Operating as previously described in Example 1, and with the same amounts of lipids and doxorubicin, the ultrasonic shaking time was extended to 10 minutes in order to obtain liposomes of size less than $1\mu$.

Since the liposomes were not perfectly homogeneous in size, a non-granular resin was used having also a molecular sieve function. 10 ml of resin, of the type known on the market as DOWEX 50-X 4 100-200 Mesh (trademark), previously activated in sodium form were therefore added.

After filtration, a suspension was obtained containing liposomes of size varying from 0.2 to $0.8\mu$ and comprising 75% of the starting doxocrubicin.

The liposomes were stabilized by lyophilization.

EXAMPLE 3

A solution of 5-fluorouracil at a concentration of 10 mg/ml in buffer phosphate 0.007N at pH 8 was poured into a saponification flask containing the lipidic phase prepared as above-described.

The suspension was treated as in Example 1, using as filtering resin 10 ml, of the type known on the market as Amberlite IRA-400 (Cl), previously activated as the hydrochloride.

The liposomes so obtained were stabilized by lyophilization.

EXAMPLE 4

The liposomes of 5-fluorouracil were prepared, operating as previously described, with the following amounts of lipids: 1.5 g of egg lecithin, 0.4 g of cholesterol, and 0.2 g of stearylamine.

As purification system, 10 ml of a resin, of the type known on the market as DOWEX 1 (50-100 mesh), previously activated, were employed.

The liposomes so obtained were stabilized by lyophilization.

EXAMPLE 5

Example 2 was repeated, except that the resin DOWEX 50W-X, 100-200 mesh, was replaced by 15 g of adsorbent resin Rohm and Haas XAD 7, and the shaking time was extended to 40 minutes.

After filtration through sintered filter glass G 1, a suspension of liposomes containing about 50% of the starting amount of doxorubicin was obtained.

The liposomes were stabilized by lyophilization.

EXAMPLE 6

1.5 g of soya-lecithin, 0.4 g of cholesterol, and 0.3 g of dicetylphosphate were dissolved in $CH_2Cl_2$ and to this solution another solution of aminosidine sulphate in 0.02M buffer phosphate at pH 6.5 at the concentration of 3 mg/ml was added.

The two phases were emulsified and as an emulsion subjected to shaking, and nitrogen was bubbled in at room temperature until complete evaporation of the methylene chloride took place.

The suspension was stabilized at room temperature for 4 hours, then into the flask was poured an amount of resin, known commercially by the trademark "IRC-50 of Rohm and Haas", equivalent to 5 g of dry resin.

After 1 hour of shaking, the liposomic suspension was filtered on a sintered glass filter to remove the resin which had retained the non-entrapped drug.

The liposomic suspension was then stabilized by lyophilization.

EXAMPLE 7

Operating as previously described in Example 6, 2.3 g of egg lecithin, 0.65 g of cholesterol and 0.15 g of octadecylamine were dissolved in 50 ml of $CH_2Cl_2$ and the solution poured into a flask containing 250 mg of m-benzoylhydratropic acid (generic name Ketoprofen) in 150 ml of Na,K buffer phosphate 0.02M at pH 7.4.

Inert gas ($N_2$) was introduced into the flask kept under shaking till complete removal of the organic solvent and the resulting formation of liposomic suspension, to which 10 ml of anion exchange resin, IRA 400 (Cl⁻) manufactured by Rohm and Haas, were added.

After 30 minutes of shaking, the resin was removed by filtration and the purified liposomic suspension lyophilized.

The following additional example is still further illustrative of the compositions of the present invention.

EXAMPLE 8

3.22 g of lecithin, 1.13 g of cholesterol, 0.956 g of dicetylphosphate and 16 mg of Vitamin E Acetate were dissolved in a small amount of $CH_2Cl_2$.

448 mg of doxorubicin HCl and 7.77 g of lactose were dissolved in a sodium phosphate 0.066M, NaCl 0.0388M, EDTA disodium salt 0.1 mM buffered solution having a pH of 5.6.

The organic and aqueous solutions were mixed and emulsified by shaking. Then nitrogen was bubbled in at room temperature until complete removal of the methylene chloride took place.

The suspension was then subjected to sonication by putting in it a sonicating probe. Then, into the flask was poured an aliquot of 80 g (wet) of ion-exchange resin, known commmercially by the trademark "IRC-50" of Rohm and Haas. After 1 hour of shaking, the resin was removed by filtration and the liposomic suspension was filtered again through a membrane filter having 3 mcm of porosity.

The liposomic suspension was then divided into vials, introduced into a freeze dryer apparatus and subjected to freeze-drying.

The vials containing the freeze-dried product were checked for purity, and the chemical and physical stability were controlled during storage at different temperatures, giving the results indicated in the accompanying Table.

provoke enlargement and leakage of the drug particles and less stability.

Note that:

our liposomic suspension consists of:
- an active drug substance selected from the Anthracycline class of antitumoral agents;
- liposomic wall components;
- hydrophilic excipients;

the liposomic wall components are selected from the following:
- phospholipids, such as lecithin or sphingomyelin or phosphatidylcholine derivatives;
- steroids, such as cholesterol;
- surfactant substances, such as dicetylphosphate or stearylamine;
- fat preservatives or anti-oxidant or antiperoxidant agents, such as alpha, beta- and gamma-tocoferols and their derivatives;

the hydrophilic excipients are selected from the following:
- complexing agents with chelating functions for metallic ions, such as EDTA (ethylenediaminetetraacetic acid) or its salts;
- buffering salts, such as phosphates or Tris (trimethylaminomethane);
- physical support to improve the tonicity of the suspension, such as sucrose, galactose, mannitol, albumin, polyethyleneglycole, dextrane, lactose, maltose, PVP, glycine, sodium chloride.

Moreover:
- the phospholipid is egg yolk- or soybean phosphatidylcholine;
- the steroid is cholesterol;
- the surfactant substance is dicetylphosphate;
- the fat preservative is Vitamin E Acetate;
- the complexing agent is EDTA sodium salt.

TABLE

| Analytical Specifications (Stability Data) Batch No. TF/22877/1 | Initial | After 1 Month | | | After 3 Months | | | After 6 Months | |
|---|---|---|---|---|---|---|---|---|---|
| | | 4° C. | Room Temp. | 35° C. | 4° C. | Room Temp. | 35° C. | 4° C. | Room Temp. |
| Appearance Freeze-Dried Cake | Compact Mass | Compact Mass | Compact Mass | Compact Mass | Compact Mass | Compact Mass | Compact Mass | Compact Mass | Compact Mass |
| Potency in Doxorubicin HCl (HPLC) | 1.857% | 1.839% | 1.879% | 1.841% | 1.865% | 1.844% | 1.723% | 1.841% | 1.653% |
| Percent of the Initial Doxorubicin Content | | 99.0 | 101.1 | 99.1 | 100.4 | 99.3 | 92.8 | 99.1 | 89.0 |
| Appearance Reconstituted Suspension | Homogeneous | Homogeneous | Homogeneous | Homogeneous | Homogeneous | Homogeneous | Homogeneous | Homogeneous | Homogeneous |
| Resuspension Time | Almost Immediately | Almost Immediately | Almost Immediately | About 1 Minute | Almost Immediately | Almost Immediately | About 1 Minute | Almost Immediately | Almost Immediately |
| pH | 5.70 | 5.71 | 5.75 | 5.75 | 5.80 | 5.79 | 5.79 | 5.76 | 5.74 |
| Non-Entrapped Doxorubicin | <5% | <5% | <5% | <5% | <5% | <5% | <5% | <5% | <5% |

Further studies on the stability of liposomes (preservation of physical and chemical properties of liposomes in storage) have yielded stability data on the freeze-dried product obtained by the process described above. These data resulted from a control performed after 6 months and are reported in the above Table.

It will be noted three different agents have been included, which are:
- a tensioactive agent (dicetylphosphate)
- a preservative (Vitamin E Acetate)
- a complexing agent (EDTA—ethylenediaminetetraacetic acid) with chelating function for metallic ions, exploits its action in preventing formation of bridges promoted by bivalent ions among liposome population by blocking lamellar fusion that might The molar ratio between phosphatidylcholine and cholesterol ranges from 0.5/1 to 10/1, and preferably from 1/1 to 3/1.

The molar ratio betwen phosphatidylcholine and dicetylphosphate ranges from 0.5/1 to 50/1, and preferably from 1/1 to 10/1.

What is claimed is:

1. A stable pharmaceutical composition consisting essentially of drug-carrying liposomes when prepared according to the process as hereinafter defined, said drug being selected from the group consisting of doxorubicin hydrochloride and aminosidine sulphate, and said process comprising:

(a) contacting a liposome suspension with an ion-exchange resin capable of selectively binding non-entrapped drug by mixing said suspension with said resin;

(b) separating said resin-bound drug from said suspension by passing said mixture through a filter medium capable of retaining said resin and filtering said suspension; and (c) stabilizing said filtrate by lyophilization.

2. The composition of claim 1, wherein said drug is doxorubicin hydrochloride.

* * * * *

UNITED STATES PATENT AND TRADEMARK OFFICE
CERTIFICATE OF CORRECTION

PATENT NO. : 4,746,516

DATED : May 24, 1988

INVENTOR(S) : Luigi MORO, Guido Neri and Alessandro RIGAMONTI

It is certified that error appears in the above-identified patent and that said Letters Patent is hereby corrected as shown below:

In the heading, insert the following:

--[30] Foreign Application Priority Data

--Sept. 30, 1977 (Italy) 28147 A/77

--Jan. 19, 1979 (Italy) 19434 A/79--

In column 1, line 30, for "steorids" read --steroids--

Signed and Sealed this

Thirteenth Day of December, 1988

Attest:

DONALD J. QUIGG

*Attesting Officer*  *Commissioner of Patents and Trademarks*